US006964682B2

(12) United States Patent
Nguyen-Thien-Nhon et al.

(10) Patent No.: US 6,964,682 B2
(45) Date of Patent: Nov. 15, 2005

(54) HEART VALVE HOLDER THAT RESIST SUTURE LOOPING

(75) Inventors: Diana Nguyen-Thien-Nhon, Santa Ana, CA (US); Myron Howanec, Jr., Corona, CA (US); Ralph Kafesjian, Newport Beach, CA (US); Delos M. Cosgrove, Hunting Valley, OH (US); Robert Stobie, Mission Viejo, CA (US); Hung Ly Lam, Norco, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 772 days.

(21) Appl. No.: 09/745,386

(22) Filed: Dec. 21, 2000

(65) Prior Publication Data

US 2002/0082686 A1 Jun. 27, 2002

(51) Int. Cl.⁷ .................................................. A61F 2/24
(52) U.S. Cl. ..................................................... 623/2.11
(58) Field of Search ....................................... 623/2.11

(56) References Cited

U.S. PATENT DOCUMENTS

| | | | |
|---|---|---|---|
| 3,409,013 A | | 11/1968 | Berry |
| 3,628,535 A | | 12/1971 | Ostrowsky et al. |
| 4,702,250 A | | 10/1987 | Ovil et al. |
| 4,865,600 A | | 9/1989 | Carpentier et al. |
| 5,476,510 A | | 12/1995 | Eberhardt et al. |
| 5,861,028 A | * | 1/1999 | Angell ....................... 623/2.11 |

FOREIGN PATENT DOCUMENTS

WO    WO 97/25004 A1    7/1997

* cited by examiner

Primary Examiner—Alvin J. Stewart
(74) Attorney, Agent, or Firm—Guy L. Cumberbatch; Debra D. Condino

(57) ABSTRACT

An improved holder, system and method for implanting a tissue-type prosthetic mitral heart valve that prevents suture looping and may also constrict the commissure posts of the valve. The holder may include two relatively movable plates, one of which attaches to the valve sewing on the inflow end of the valve ring and the other which attaches via sutures or similar expedient to the valve commissures on the outflow end. Separation of the plates places the sutures in tension and constricts the commissures. The sutures may be strands or filaments, or may be wider bands of flexible biocompatible material. If bands are used, they desirably cover the commissure post tips to further help prevent suture looping thereover. The flexible lengths of material extend directly between commissures of the valve, or may extending radially inward from each commissure to a central upstanding member. Desirably, a slide is created by the flexible lengths of material adjacent each commissure post, for example by crossing over suture filaments at or radially inward from the commissure posts. If an upstanding member is used, the lengths of suture extend axially beyond the commissure post tips to create a tent that wards off sutures that otherwise might loop around the tips during advancement of the valve along an array of pre-implanted sutures.

10 Claims, 5 Drawing Sheets

HEART VALVE HOLDER THAT RESIST SUTURE LOOPING

FIELD OF THE INVENTION

The present invention relates generally to medical devices, and more particularly to an apparatus for facilitating the implantation of a bioprosthetic replacement heart valve, particularly a mitral valve, and associated methodology.

BACKGROUND OF THE INVENTION

In mammalian animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves and have leaflets to control the directional flow of blood through the heart. The valves are each mounted in an annulus that comprises a dense fibrous ring attached either directly or indirectly to the atrial or ventricular muscle fibers. Various surgical techniques may be used to repair a diseased or damaged valve. In a valve replacement operation, the damaged leaflets are excised and the annulus sculpted to receive a replacement valve.

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is constructed with natural-tissue valve leaflets which function much like a natural human heart valve's, imitating the natural action of the flexible heart valve leaflets which form commissures to seal against each other to ensure the one-way blood flow. In tissue valves, a whole xenograft valve (e.g., porcine) or a plurality of xenograft leaflets (e.g., bovine pericardium) provide occluding surfaces that are mounted within a surrounding stent structure. In both types of prosthetic valves, a biocompatible cloth-covered sewing or suture ring is provided on the valve body, for the mechanical type of prosthetic valve, or on the inflow end of the stent for the tissue-type of prosthetic valve.

In placing a tissue type prosthetic valve in the mitral position, the commissure posts are on the blind side of the valve and may become entangled with pre-installed sutures, and may damage the annulus or tissue during delivery. The difficulty of the delivery task is compounded if the surgery is through a minimally-invasive access channel, a technique that is becoming more common. The problem of entanglement is termed "suture looping," and means that the suture that is used to attach or mount the valve to the heart tissue is inadvertently wrapped around the inside of one or more of the commissure post tips. If this occurs, the looped suture may damage one of the tissue leaflets when tightly tied down, or at least may interfere with the implant procedure or valve operation and prevent maximum coaptation of the valve leaflets, resulting in a deficiency in the prosthetic mitral valve.

Some attempts have been made to overcome these problems in current holders for prosthetic mitral valves. An example of such a holder is U.S. Pat. No. 4,865,600, Carpentier, et al., incorporated herein by reference. Carpentier provides a holder having a constriction mechanism that constricts the commissure posts inwardly prior to implantation. The Carpentier device provides an elongate handle to both hold the valve/valve holder combination during implantation, as well as to cause the commissure posts to constrict inwardly. The valve is connected to the valve holder by the manufacturer using one or more sutures, and the combination shipped and stored as a unit. During the valve replacement procedure, the surgeon connects the handle to the holder and locks a locking nut to hold the commissure posts at a given constricted position. The surgeon then attaches the sewing ring of the valve to the native valve annulus with an array of sutures that has been pre-embedded in the annulus and extended outside the body. The valve is then advanced along the array of sutures to its desired implantation position and the sutures tied off. When the holder is cut free, the commissure posts are released to expand and the holder may be removed using the handle. However, even when the commissure posts are constricted, slack in the array of sutures, for example, may lead to looping of sutures around one of the cloth-covered commissure posts, which interferes with the implantation procedure.

What is needed then is an improved tissue-type prosthetic valve holder attachable to the inflow end of the valve that insures against suture looping.

SUMMARY OF THE INVENTION

The present invention provides a holder for a tissue-type prosthetic heart valve having an inflow end and an outflow end and a flow axis therebetween. The valve includes an annular suture ring at the inflow end attached to a stent having posts circumferentially-spaced about the flow axis that support occluding tissue surfaces of the valve. In this type of valve the posts are cantilevered generally in the outflow direction.

The present invention provides an improved holder system for preventing suture looping around the commissure posts of tissue-type heart valves that are implanted in the direction where the commissure posts form the leading end of the valve. For instance, the present invention provides an improved holder for a mitral valve. In general, the invention provides improvements to an arrangement of lengths of flexible material extending between the commissure posts of the valve. Each length of flexible material extends axially, desirably through the valve, to be connected at two points to a rigid holder structure that abuts the inflow end of the valve. Severing the lengths of flexible material near one of the attachment points permits removal of the entire length of material from the valve along with the rigid structure, by virtue of the second attachment point. In a preferred embodiment, the rigid structure incorporates a mechanism for pulling the lengths of flexible material to cause the commissure posts of the valve to flex inward.

In one particular embodiment, a holder is provided that includes a plurality of lengths of flexible material extending in a taut fashion across the outflow end of the valve to prevent suture looping, each length of material having a first segment extending directly between adjacent commissure posts and crossing over each adjacent length of material adjacent to the commissure post. The lengths of flexible material may be sutures, or may comprise a band of biocompatible material, such as polyester. In the latter instance, the band of material may completely cover each commissure post, and may cross over adjacent bands of material.

In another embodiment of the invention, the holder includes a plurality of lengths of flexible material extending in a taut fashion across the outflow end of the valve to prevent suture looping, each length of material having a first segment extending in a band that a substantially wider than it is thick directly between adjacent commissure posts. Each length of flexible material may extend in second segments along two adjacent commissure posts to be attached to the rigid structure at two points. Desirably, the commissure posts are cloth covered and the second segments pass beneath the cloth covering in a configuration that is not as wide as the first segments.

In a further aspect of the present invention, the holder includes a central upstanding member passing along the axis of the valve from the inflow side to the outflow side of the leaflets. A plurality of lengths of flexible material extend in a taut fashion across the outflow end of the valve to prevent suture looping, each length of flexible material having first segments extending radially inward from one of the commissure posts to the central upstanding member. The central upstanding member may be hollow, with each length of flexible material passing into and through the member.

Alternatively, the upstanding member may be solid and include notches for receiving midpoints of the first segments of lengths of flexible material. In this case, each first segment extends from one of the commissure posts radially inward to the upstanding member and then radially outward to an adjacent commissure post via a notch. The upstanding member may include a wide base on an end that is attached to a rigid structure of the holder that abuts the sewing ring. A narrow shaft extends from the wide base and passes between and to the outflow side of the leaflets. The narrow shaft may have a non-circular cross-section, such as triangular, to reduce deformation of the leaflets from long-term storage.

The holder may include a valve abutment portion sized and shaped to abut the suture ring at the inflow end of the valve. The holder may further include a commissure post constriction mechanism adapted to constrict the commissure posts radially inward from a relaxed position to a constricted position when actuated by a handle adapted to operatively connect to the commissure post constriction mechanism. A retaining mechanism may also be provided that retains the commissure post constriction mechanism in the constricted position after the handle is removed.

In one embodiment the commissure post constriction mechanism comprises an adjusting portion and an adjusting member adapted to adjust the distance between the adjusting portion and the valve abutment portion and one or more filaments attached to the adjusting portion and sutured through the end of the commissure posts distal the adjusting portion. When the adjusting member is operated to separate the adjusting portion from the valve abutment portion the adjusting portion pulls the filaments, which in turn urge the end of the commissure posts distal the adjusting portion radially inwardly, to the constricted position.

The valve abutment portion may be of a planar shape, with the adjusting portion of a substantially complementary planar shape to the valve abutment portion. It is preferred that the planar shape of the valve abutment portion be comprised of a plurality of tangs radiating from a central body to each cover a portion of the suture ring. In this manner a sufficient amount of the suture ring is left exposed to allow for suturing the suture ring to the native annulus.

Adjustment of the distance between the valve abutment portion and the adjusting portion may be achieved by providing a central threaded aperture in the adjusting portion and an adjusting member that cooperates with this threaded aperture. In this construction the end of the adjusting member proximal the valve abutment portion abuts the valve abutment portion during operation. When the adjusting member is advanced through the central aperture of the adjusting portion it pushes the valve abutment portion and the two portions separate.

A handle may be operatively connected to the adjusting member to turn it by providing a handle that has an externally threaded end portion and an adjusting member having a central longitudinal threaded bore sized to receive the threaded end of the handle. When the handle is introduced into the bore it is rotated in a first direction and will seat in the threaded bore of the adjusting member. Further rotation of the adjusting member separates the adjusting portion from the valve abutment portion, as recited above, and causes the commissure posts to constrict inwardly.

A further understanding of the nature and advantages of the present invention are set forth in the following description and claims, particularly when considered in conjunction with the accompanying drawings in which like parts bear like reference numerals.

DESCRIPTION OF THE PREFERRED EMBODIMENTS

The present invention provides an improved heart valve holder for tissue-type prosthetic heart valves that facilitates implantation and reduces the chance of suture entanglement. The holder of the present invention is particularly useful for prosthetic mitral heart valves having commissure posts on the outflow side supporting flexible leaflets therebetween. The mitral position is such that the outflow side (and commissure posts) projects distally toward the left ventricle during implantation, and thus the holder must be attached to the inflow (i.e., accessible) side of the valve. Delivery of the valve to the mitral position involves sliding the valve down a plurality or array of sutures that have been pre-installed around the annulus and then passed through the valve sewing ring. The holder of the present invention constricts the commissure posts radially inward and thus helps prevent the posts from becoming entangled in the array of pre-installed sutures. This benefit is thus especially advantageous where the outflow side and commissure posts of the heart valve extend distally during delivery, forming the leading end of the valve, which is the case in a prosthetic mitral valve implantation. Nonetheless, the holder of the present invention may prove useful for the implantation of heart valves in other than the mitral position, and thus the invention may be applicable thereto.

Figure 1:
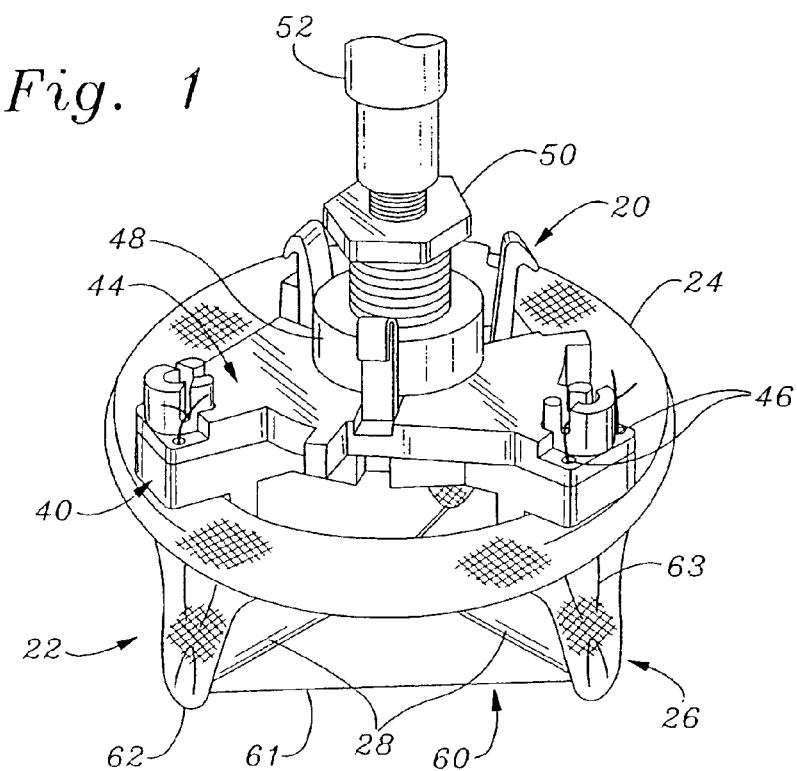
FIG. 1 is a perspective view of a heart valve holder of the present invention assembled to the inflow side of a tissue-type heart valve.

With reference now to FIG. 1 an exemplary holder 20 of the present invention is shown attached to a tissue-type heart valve 22. The heart valve 22 includes an annular sewing ring 24 on an inflow side, and a plurality of commissure posts 26 projecting generally axially in the outflow direction. The holder 20 attaches to the sewing ring 24 on the inflow side of the valve 22, which also is the proximal (i.e., accessible) side during implantation. That is, the commissure posts 26 project distally toward the outflow side of the valve 22, defining the leading end of the valve during implantation.

The heart valve 22 further includes a plurality of flexible leaflets 28 that are supported by and extend between the commissure posts 26. The leaflets 28 provide the occluding surfaces of the valve 22, and may be made of individual pieces of bovine pericardium, for example. Alternatively, the leaflets 28 may be part of an entire xenograft, or homograft. In the former instance, natural porcine (pig) valves are particularly useful. Therefore it should be understood that the leaflets 28 may be formed of a variety of materials, none of which is limiting with respect to the present invention. In addition, there are preferably three such leaflets 28 corresponding to three commissure posts 26.

Various constructions for the heart valve 22 are known, which may include metallic or plastic stent elements, a silicone or urethane insert for the sewing ring 24, biocompatible fabric (i.e., polyester) covering around one or more of the elements, etc. In a preferred embodiment, the heart valve 22 includes an internal metallic wireform (not shown) having an undulating shape with a plurality of arcuate cusps connected by upstanding commissures. The wireform commissures provide internal structure for the commissure posts 26 of the valve, and are somewhat flexible so as to be able to flex or cantilever inward. The holder 20 of the present invention facilitates this flexing, though the invention may be practiced in its broadest sense without causing inward movement of the commissure posts. It should be noted that other internal constructions of heart valve 22 having movable commissure posts are available with which the holder 20 of the present invention may function equally as well.

An exemplary holder 20 of the present invention includes a rigid structure of three relatively movable elements. A plate-like valve abutment portion 40 lies against the inflow side of the sewing ring 24, and includes a plurality of through holes around its periphery. A plate-like commissure adjusting portion 44 generally mirrors the shape of the valve abutment portion 40, and also includes a plurality of peripheral through holes 46. The adjusting portion 44 further includes a centrally located and internally threaded boss 48 that projects in a proximal direction from the otherwise generally planar adjusting portion. Finally, an adjusting member 50 having external threads thereon is sized to mate with the internal threads of the boss 48. It should be understood that the function of the holder 20 in constricting the valve commissures may be accomplished with different structures than the one shown.

Figure 3:
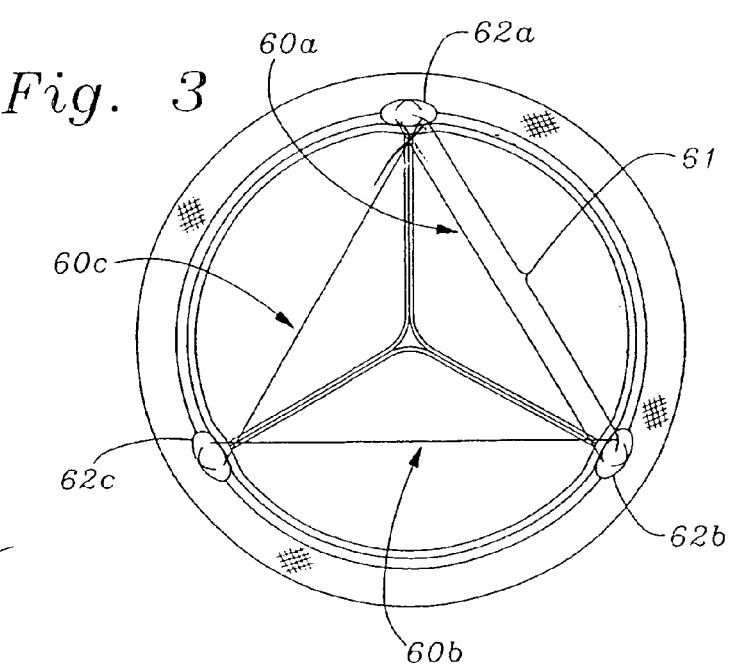
FIG. 3 is a cutaway perspective view of one of the commissures of the valve shown in FIG. 1.
Figure 2:
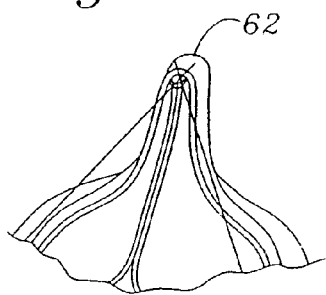
FIG. 2 is a plan view of the outflow end of the valve and holder of FIG. 1.

A plurality of lengths of flexible material 60 is shown in FIGS. 1–3 partly extending between the tips 62 of the commissure posts 26. In the preferred embodiment, the lengths of flexible material 60 comprise mono- or polyfilament sutures, and that exemplary nomenclature will be used herein. Because there are three commissure posts 26, there are at least three lengths of sutures 60 extending therebetween in an equilateral triangular configuration. Each length of suture 60 includes a first segment 61 spanning between two of the commissure posts 26. Second segments 63 of each length of suture 60 extend axially in a proximal direction from the tips 62 and along the post 26, the segments passing through the sewing ring 24 and attaching to the holder 20. This is seen best in the perspective view of FIG. 1. Specifically, both second segments 63 pass through the holes in the valve abutment portion 40 and attach to the adjusting portion 44 at discrete attachment points, for example by tying the free ends of each suture. In this manner, each length of suture 60 may be severed close to one of its points of attachment to the adjusting portion 44 and pulled free of the valve 22 along with the holder 20 by virtue of its remaining attachment point. Further specifics of this arrangement can be seen in co-pending U.S. application Ser. No. 09/626,570, filed Jul. 27, 2000, and in a continuation-in-part of the 09/626,570 application filed on even date herewith, the entire disclosures of which are hereby expressly incorporated by reference.

As mentioned, the abutment portion 40, adjusting portion 44, and adjusting member 50 are relatively movable. That is, the adjusting portion 50 is adapted to cause relative axial displacement between the abutment portion 40 and the adjusting portion 44 (preferably by connecting a handle 52 thereto). Because the abutment portion 40 remains against the sewing ring 24, the adjusting portion 44 translates proximally away from the abutment portion, and attached valve 22. Because the lengths of suture 60 attach to the adjusting portion 44, they are also pulled in the proximal direction. Moreover, because the first segment 61 of each length of suture 60 spans between two of the commissure posts 26, proximal movement of the adjusting portion 44 and attached second segments 63 causes radially inward movement of the tips 62, with the commissure posts 26 generally flexing inward from their structural point of attachment within the valve 22 adjacent the sewing ring 24.

It should be clearly understood that the inward flexing of the commissure post tips 62 reduces the chance of suture looping around the tips, but that certain aspects of the present invention reduce suture looping even without tip flexing. That is, the lengths of suture 60 may attach to the rigid structure of a holder that simply abuts the valve, without the relatively moving elements that cause commissure deflection.

With reference to FIGS. 1–3, the arrangement of the discrete lengths of sutures 60 will now be described. There are desirably three equal lengths of suture 60, each secured at its two free ends to the adjusting portion 44. As mentioned, the second segments 63 pass through the aligned holes 46 in the adjusting portion 44 and abutment portion 40, and then through the sewing ring 24 to a first commissure post 26. From there, the second segments 63 continue generally axially to the tips 62 of adjacent commissure posts 26, and the first segment 61 spans obliquely across the outflow side of the valve 22 structurally coupling the two tips. It should be noted that each of the commissure posts 26 desirably has a fabric covering, and the lengths of suture 60 pass at least once through the fabric covering at the tip 62 or along each post 26. For example, FIG. 3 shows the first segments 61 passing below the fabric covering at the tip 62, and FIG. 1 shows the second segments 63 threading at least once through the fabric. This threaded path guides the lengths of suture 60 along their predetermined paths. It is a simple matter to remove the lengths of suture 60 from the valve 22 along with the holder by puling them free from the fabric cover.

As seen best in FIGS. 2 and 3, the first segment 61 of each length of suture 60 extends from a circumferential side of the respective commissure post tip 62 that is farthest away from the destination tip. That is, three lengths of sutures 60a, 60b, 60c are seen in FIG. 2 extending between three commissure post tips 62a, 62b, 62c, using a clockwise nomenclature. The first segment 61 of the first length of suture 60a extends from a counter-clockwise side of the first commissure post tip 62a to a clockwise side of the second suture post tip 62b. The other two lengths of sutures are arranged accordingly such that each two adjacent lengths of suture cross over (i.e., intersect) just prior to being threaded into (i.e., just radially inward from) the respective commissure post tips 62. This intersection of the sutures 60 defines a plane or slide closely adjacent to each commissure post tip 62. The plane or slide formed by the crossed sutures 60 helps prevent suture looping because a barrier of sorts is provided that guides loose sutures over each post tip 62.

As mentioned and as seen in FIG. 1, the second segment 63 of each length of suture 60 continues axially along the respective commissure posts 26 and may be threaded into and out of the cloth covering thereover. Desirably, a second crossover of the second segments 63 is provided in the commissure posts 26 to insure that each end is secured to the adjusting portion 44 in the proper orientation. As seen in FIG. 1, therefore, the length of suture 60 that is seen extending between the two visible commissure posts 26 extends upward through the valve 22 and holder 20 to emerge from the closest aligned holes 46 (as shown) and be secured in the cutting guide. This dual crossover thus helps a surgeon identify which lengths of sutures 60 extend between which commissure posts 26.

Figure 4:
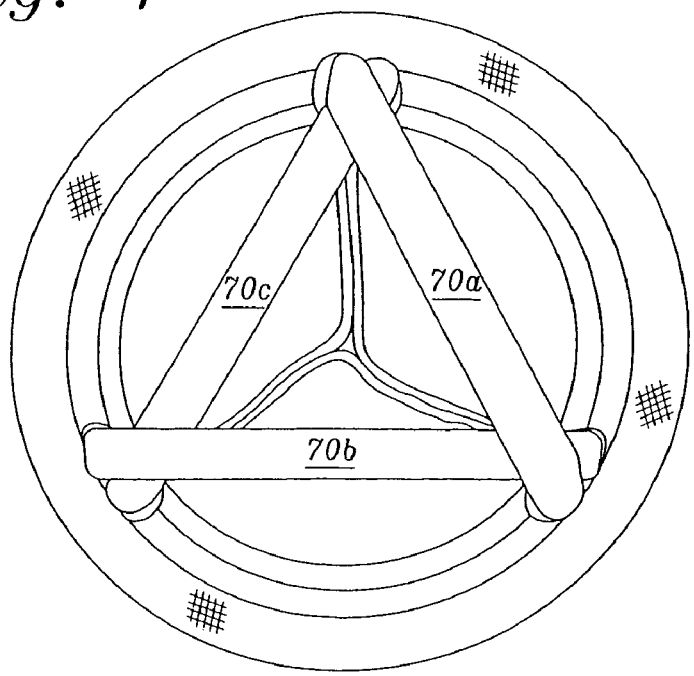
FIGS. 4 and 5 are outflow plan and perspective views, respectively, of an alternative heart valve and holder of present invention.
Figure 5:
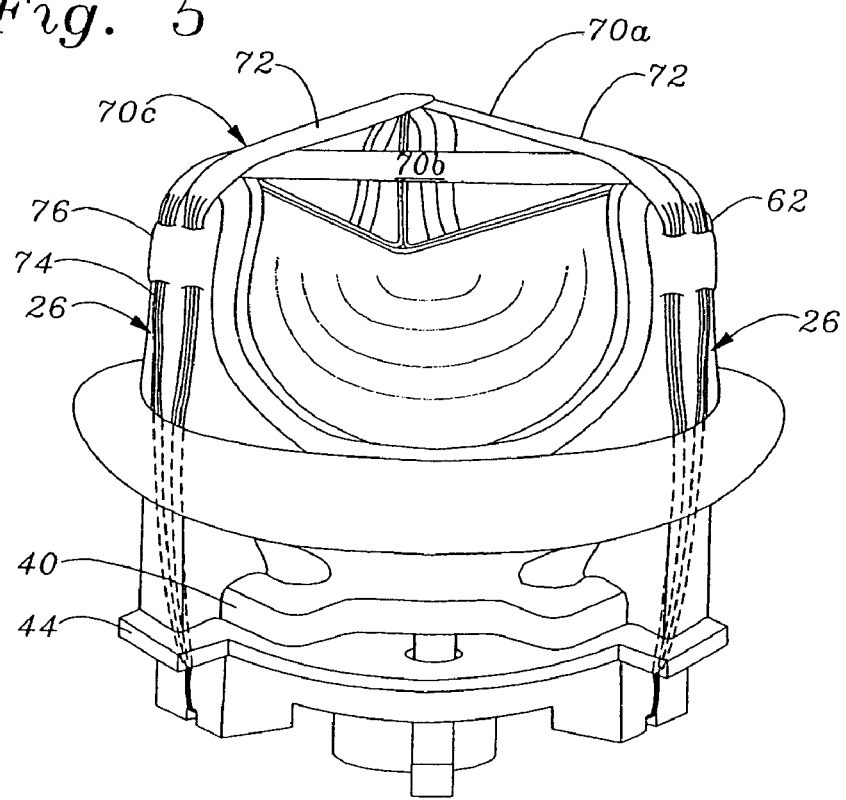

FIGS. 4 and 5 illustrate a second embodiment of heart valve holder of the present invention for preventing suture looping which also provides a planar guard over the commissure tips, similar to the crossed-over lengths of filament-like material of FIGS. 1–3. In general, the holder of FIGS. 4–5 is identical to the holder described above, with the substitution of flexible bands 70a, 70b, 70c instead of lengths of suture 60. The bands 70 may be made of polyester tape, or other suitable biocompatible material similar to sutures. In one embodiment, the bands 70 are substantially wider than they are thick (e.g., formed in a tape or flat strip), and desirably have a width that is approximately equal to the circumferential width of the each of the commissure post tips 62.

As seen best in FIG. 5, first segments 72 of the bands 70 extend between the commissure post tips 62 in a flattened configuration and cross over each adjacent band at or slightly inward from the tip. After extending to the outside of the commissure post tip 62, each band 70 is folded, twisted, or otherwise narrowed in second segments 74 to pass through one or more fabric tunnels 76 along the commissure posts 26. Ultimately, each narrowed second segment 74 passes through aligned holes in the abutment portion 40 and adjusting portion 44 and is secured to the adjusting portion, as described above. The mechanism for the holder 20 of FIGS. 4–5 is similar to that described above in that separation of the abutment portion 40 and adjusting portion 44 pulls the narrowed second segments 74 of the bands 70 to shorten the flattened first segments 72 between the commissure post tips 62. As each second segment 74 is pulled, the first segment 72 follows and is folded or otherwise narrowed as it passes through the fabric cover of the commissure post 26. Moreover, when the holder is removed, one of the second segments 74 of each band 70 is severed close to its point of attachment to the holder and the band 70 may then be pulled free from the valve by virtue of its remaining attachment to the holder. In this regard, the bands 70 may be TEFLON (PTFE) to facilitate sliding through the fabric tunnels in the valve.

Because of the flattened or otherwise planar configuration of the bands 70, suture looping around the commissure post tips 62 is greatly reduced. That is, sutures that contact the bands 70 will be guided over and to the outside of each commissure post tip 62. The bands 70 provide slides of sorts that guide the loose sutures over the commissure post tips 62, and in the preferred embodiment, the bands completely cover the tips to present a smooth, even surface.

Figure 6:
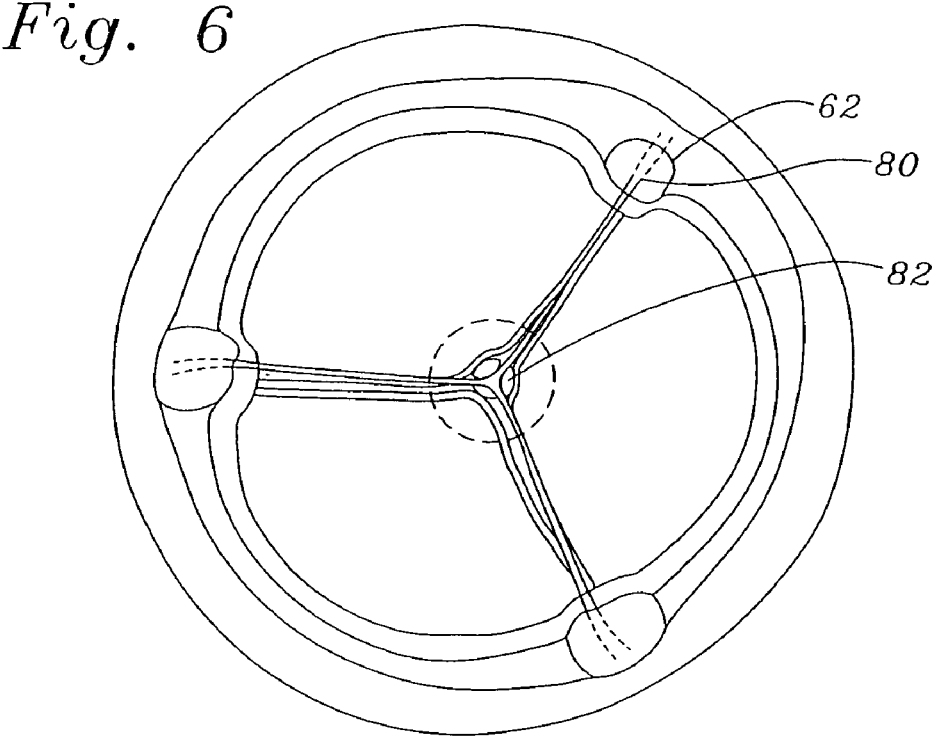
FIGS. 6 and 7 are outflow plan and perspective views, respectively, of a further alternative heart valve and holder of present invention having a central upstanding member.
Figure 7:
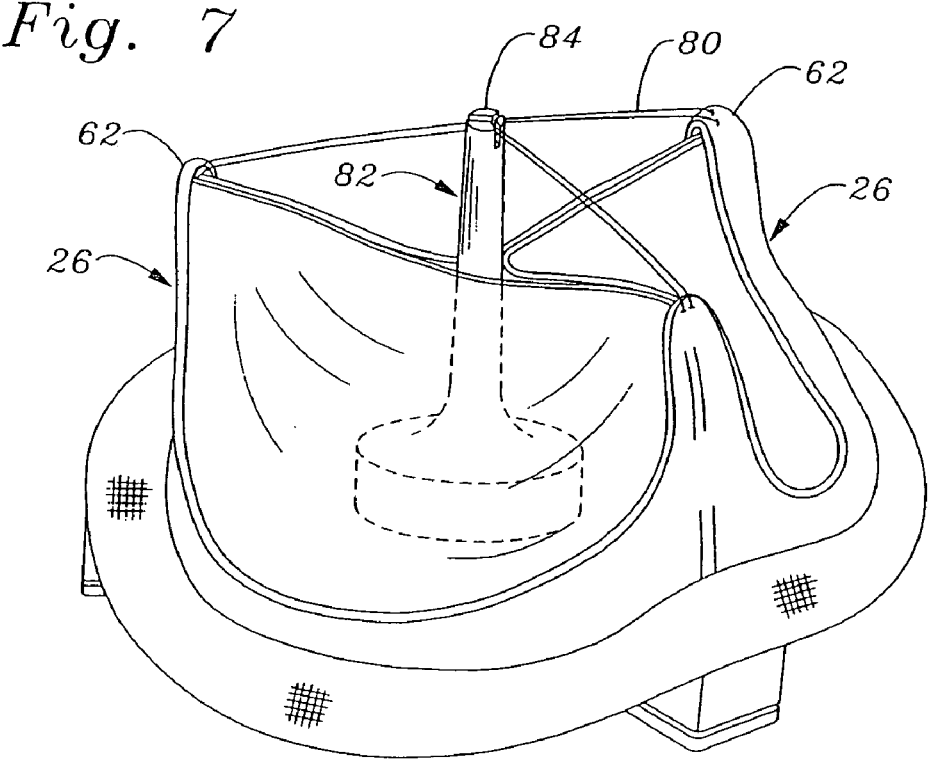

FIGS. 6–8 illustrate a further embodiment of a heart valve holder for preventing suture looping. As seen best in FIG. 7, a plurality of lengths of sutures 80 extends between the commissure post tips 62 across the outflow side of the valve as before, although first to a central upstanding member 82 elevating the lengths of sutures above the commissure post tips. The upstanding member 82 has an upper end 84 with a plurality of grooves or notches therein through which the lengths of suture 80 are threaded. Although the upstanding member 82 is shown as being elevated axially beyond the commissure post tips 62, some of the benefits of reduced suture looping may be realized if the member has the same axial height as the post tips.

Figure 8B:
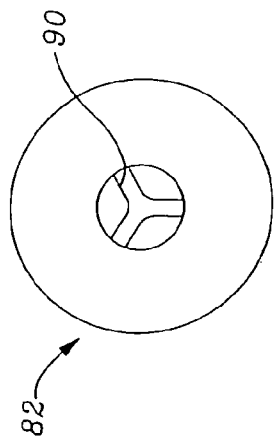
FIGS. 8A–8C are several views of the upstanding member of the holder of FIGS. 6 and 7.
Figure 8C:
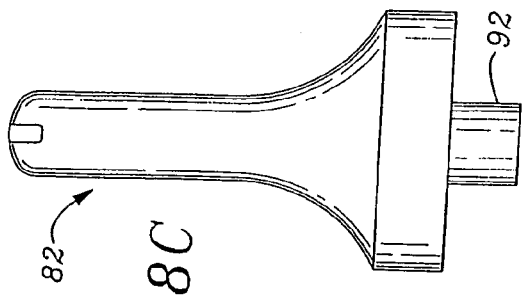
Figure 8A:
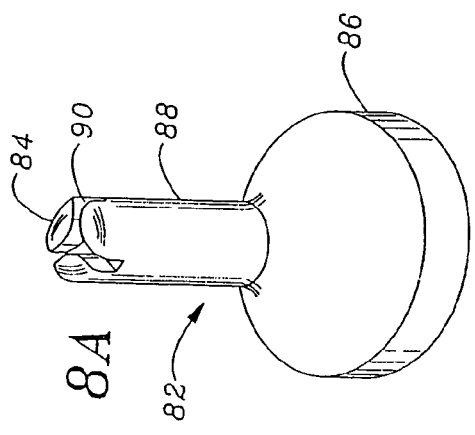

An exemplary embodiment of the upstanding member 82 is illustrated in FIGS. 8A–8C. The member 82 includes a wide base 86 and a narrow shaft 88 terminating in the upper end 84. Three generally radial grooves 90 are formed in the upper end 84 distributed about 120 degrees with respect to each other. These grooves 90 are each aligned with one of the commissure post tips 62 to receive a length of suture 80 extending therefrom. A lower pin 92 in the upstanding member 82 fits within a central bore provided in the center of the abutment portion 40. Alternatively, the upstanding member 82 may be integrally molded with the abutment portion 40. The wide base 86 strengthens the upstanding member 82, and the shaft 88 has a length that projects axially above the commissure posts 26.

As seen in FIG. 7, threading the lengths of suture 80 through the grooves 90 in the upper end 84 of the upstanding member 82 provides a tent of sorts. This suture tent helps to prevent suture looping around the commissure post tip 62. That is, errant sutures that contact any of the angled lengths of suture 80 are guided up and over the nearest commissure post tip 62.

Figure 8D:
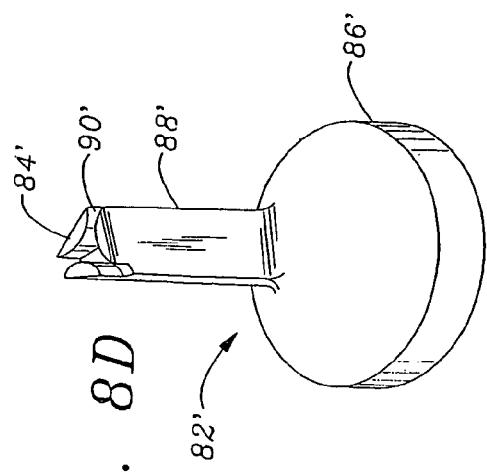
FIG. 8D is a perspective view of an alternative upstanding member of the holder of FIGS. 6 and 7 having a triangular cross-section.

An alternative embodiment of an upstanding member 82' is illustrated in FIG. 8D. As in the earlier embodiment, the member 82' includes a wide base 86' and a narrow shaft 88' terminating in an upper end 84' having three generally radial grooves 90' distributed about 120 degrees with respect to each other. The shaft 88' has a triangular as opposed to circular cross-section so as to better mate with the surrounding leaflets in the assembly of the valve and holder. That is, the three leaflets come together in an equilateral triangle, desirably at the axis of the valve, and the upstanding member 82' will be oriented such that the corners of the triangular shaft 88' project toward each valve commissure, thus bifurcating two leaflets. In this way the midpoint of each leaflet free edge abuts the flat sides of the shaft 88', minimizing any deformation of the leaflet at that midpoint from the extended contact with the shaft 88' during long term storage in a preservative solution.

Figure 9:
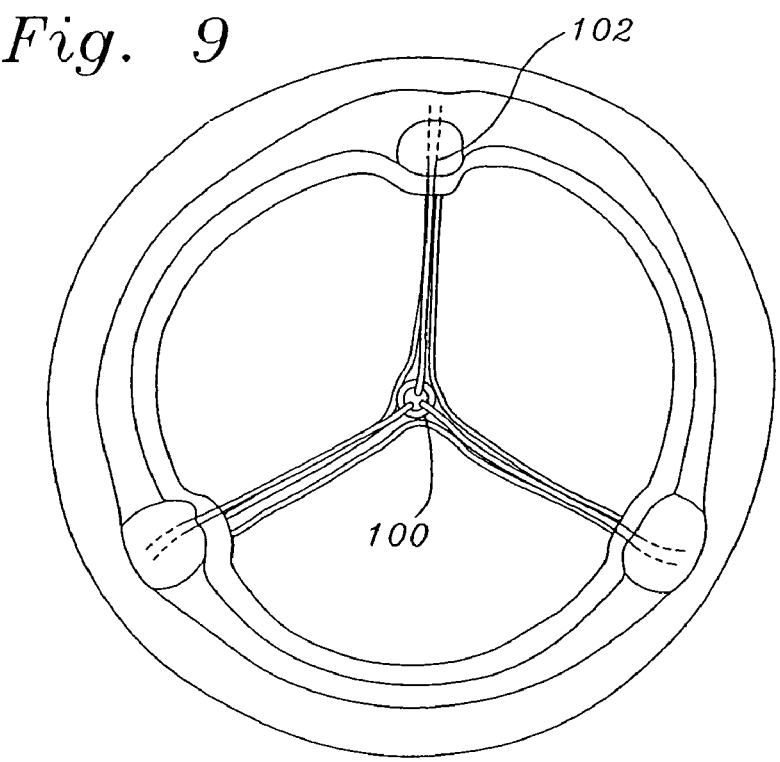
FIGS. 9 and 10 are outflow plan and perspective views, respectively, of a still further alternative heart valve and holder of present invention having a hollow central upstanding member.
Figure 10:
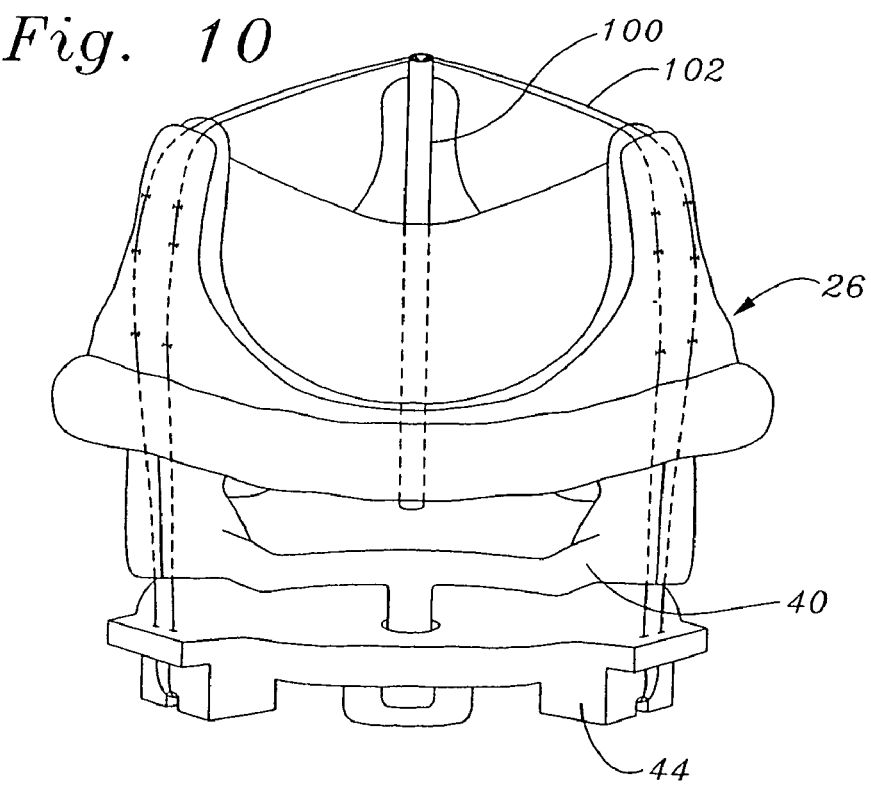

FIGS. 9 and 10 illustrate a further heart valve holder of the present invention that also makes use of a central upstanding member 100, although the member is hollow and the lengths of suture 102 extend axially through the member to be connected to either the abutment portion 40 or adjustment portion 44. The lengths of suture 102 may be filaments or strands, or may be wider bands as described above with respect to FIGS. 4–5. The upstanding member 100 maybe a hollow tubular structure fastened within or molded with the abutment portion 40. Again, the axial height of the upstanding member 100 is greater than the axial height of the commissure posts 26 such that the lengths of suture 102 are tented across the outflow end of the valve It will be appreciated that the invention has been described hereabove with reference to certain examples or preferred embodiments as shown in the drawings. Various additions, deletions, changes and alterations may be made to the above-described embodiments and examples without departing from the intended spirit and scope of this invention. Accordingly, it is intended that all such additions, deletions, changes and alterations be included within the scope of the following claims.

What is claimed is:

1. A holder for a tissue-type prosthetic heart valve attachable to a surgical delivery handle, the heart valve having an inflow end and an outflow end and a flow axis therebetween, the valve including an annular suture ring at the inflow end and a plurality of generally axially-extending commissure posts circumferentially-spaced around the outflow end that support occluding tissue surfaces of the valve, the holder comprising:

a plurality of lengths of flexible material extending in a taut fashion across the outflow end of the valve to prevent suture looping, each length of material having a first segment extending directly between adjacent commissure posts and crossing over (i.e., intersecting each adjacent length of material just radially inward from the commissure post therebetween.

2. The holder of claim 1, wherein the lengths of flexible material comprise lengths of suture.

3. The holder of claim 1, the holder further including a rigid structure that abuts the annular sewing ring at the inflow end of the valve, the lengths of flexible material each axially extending in second segments along two adjacent commissure posts and attaching to the rigid structure at two points such that each length may be severed close to one of its points of attachment to the rigid structure and pulled free of the valve along with the rigid structure by virtue of its remaining attachment point.

4. The holder of claim 3, wherein the rigid structure includes a mechanism for pulling the second segments toward the rigid structure causing the first segments to shorten and the commissure posts to flex inward toward each other.

5. The holder of claim 1, wherein the first segment of each length of flexible material comprises a band that is substantially wider than it is thick.

6. The holder of claim 5, the holder further including a rigid structure that abuts the annular sewing ring at the inflow end of the valve, the three lengths of flexible material each axially extending in second segments along two adjacent commissure posts and attaching to the rigid structure at two points such that each length may be severed close to one of its points of attachment to the rigid structure and pulled free of the valve along with the rigid structure by virtue of its remaining attachment point.

7. The holder of claim 6, wherein the commissure posts are cloth covered, and wherein the second segments pass beneath the cloth covering of the respective commissure posts, the second segments having a configuration that is not as wide as the first segments.

8. The holder of claim 5, wherein the band is TEFLON.

9. The holder of claim 1, wherein the lengths of flexible material each axially extend in second segments along two adjacent commissure posts and attach to a rigid structure that abuts the annular sewing ring at the inflow end of the valve, wherein the second segments of two adjacent lengths of flexible material cross over a second time along the common commissure post prior to attaching to the structure.

10. The holder of claim 9, wherein each length of flexible material attaches to the rigid structure at two points such that each length may be severed close to one of its points of attachment to the rigid structure and pulled free of the valve along with the rigid structure by virtue of its remaining attachment point.

* * * * *